United States Patent [19]

Leir

[11] Patent Number: 4,617,396

[45] Date of Patent: Oct. 14, 1986

[54] PROCESS FOR THE PREPARATION OF DERIVATIVES OF PIPERIDINE

[75] Inventor: Charles M. Leir, New Richmond, Wis.

[73] Assignee: Riker Laboratories, Inc., St. Paul, Minn.

[21] Appl. No.: 772,474

[22] Filed: Sep. 4, 1985

Related U.S. Application Data

[63] Continuation of Ser. No. 269,068, Jun. 2, 1981, abandoned, which is a continuation of Ser. No. 162,312, Jun. 23, 1980, abandoned, which is a continuation of Ser. No. 21,332, Mar. 19, 1979, abandoned.

[51] Int. Cl.$^4$ ............................................ C07D 211/26
[52] U.S. Cl. .................................... 546/233; 546/224; 562/419
[58] Field of Search ................. 546/224, 233; 562/419

[56] References Cited

U.S. PATENT DOCUMENTS

| | | | |
|---|---|---|---|
| 3,419,595 | 12/1968 | Hansen | 260/456 R |
| 3,655,728 | 4/1972 | Mendel | 514/544 |
| 3,900,481 | 8/1975 | Banitt et al. | 546/224 |

OTHER PUBLICATIONS

Van Arendonk, A., et al., *J. Am. Chem. Soc.*, 53, 3184–6, (1931).
Beilstein's *Handbuch der Organischen Chemie*, 3rd Supp., vol. 7, Part 2, Springer-Verlag, Berlin, 1968, p. 936.
Trahanovsky, W., et al., *Tett. Lett.* No. 18, 2155–2158 (1968).
McKillop, A., et al., *Syn. Comm.*, 4(1), 35–43 (1974).
Bacon, R., et al., *J. Chem. Soc.* (C), 1969, pp. 312–315.
March, J., *Advanced Organic Chemistry*, 2nd Ed., McGraw-Hill, New York, 1977, pp. 244, 324.
G. A. Dafforn, et al., *Tetrahedron Letters* 36, 3159–3162 (1970).
J. T. Gupton, et al., *Synthetic Communications* 12, 695–700 (1982).
Raber, D., et al., *Tetrahedron Letters*, 8, 667–670 (1974).
Bentley, M., et al., *Tetrahedron Letters* 10, 741–744 (1971).
D. E. Pearson, et al., *Chemical Reviews* 74, 46 (1974).
F. L. Scott, *Chemistry and Industry*, 224 (1959).

*Primary Examiner*—Richard A. Schwartz
*Attorney, Agent, or Firm*—Donald M. Sell; James A. Smith; Robert W. Sprague

[57] ABSTRACT

Processes for the preparation of the antiarrhythmic agent 2,5-bis(2,2,2-trifluoroethoxy)-N-(2-piperidylmethyl)benzamide.

4 Claims, No Drawings

PROCESS FOR THE PREPARATION OF DERIVATIVES OF PIPERIDINE

This is a continuation of application Ser. No. 269,068 filed June 2, 1981, now abandoned, which is a continuation of application U.S. Ser. No. 162,312 filed June 23, 1980, now abandoned, which is a continuation of application U.S. Ser. No. 21,332 filed Mar. 19, 1979, now abandoned.

This invention relates to an improved process for the preparation of certain antiarrhythmic agents in which a carbon atom of a piperidine or pyrrolidone ring is bonded directly or through a methylene group to the nitrogen of a substituted benzamido group from bromo- or hydroxy-substituted benzenes.

The antiarrhythmic compounds which are the products of this process and a process for their preparation are described in U.S. Pat. No. 3,900,481.

The present process is preferred to that of the prior art due to various practical advantages, e.g. the relatively low cost of the starting material, the ease of carrying out the unit operations therein and the relatively high yields of the desired products (particularly as it relates to the preparation of the 2,5-distributed compounds of U.S. Pat. No. 3,900,481).

TECHNICAL FIELD

This invention relates to processes for preparing certain antiarrhythmic agents.

SUMMARY OF THE INVENTION

In one aspect of the invention, a method of preparing a 2,5-bis(2,2,2-trifluoroethoxy)-N-(2-piperidylmethyl)-benzamide is provided which comprises the following steps. Hydroquinone is contacted with 2,2,2-trifluoroethyl trifluoromethanesulfonate under conditions to yield 1,4-bis(2,2,2-trifluoroethoxy)benzene. Then, in the presence of a Lewis acid catalyst, the 1,4-bis(2,2,2-trifluoroethoxy)benzene is treated with an acetylation agent under conditions to create 2,5-bis(2,2,2-trifluoroethoxy)acetophenone. The methyl moiety of the acetophenone function of the 2,5-bis(2,2,2-trifluoroethoxy)acetophenone is thereafter replaced using hypochlorite to yield 2,5-bis(2,2,2-trifluoroethoxy)benzoic acid. The 2,5-bis(2,2,2-trifluoroethoxy)benzoic acid is then treated with an inorganic chloride to provide 2,5-bis(2,2,2-trifluoroethoxy)benzoic acid chloride. Subsequently, the resultant 2,5-bis(2,2,2-trifluoroethoxy)benzoic acid chloride is contacted with 2-aminomethylpyridine, whereby there is formed 2,5-bis(2,2,2-trifluoroethoxy)-N-(2-pyridylmethyl)benzamide. Finally, the 2,5-bis(2,2,2-trifluoroethoxy)-N-(2-pyridylmethyl)benzamide is treated with an agent capable of hydrogenation of the aromatic bond in the heterocyclic ring, whereby there is formed a 2,5-bis(2,2,2-trifluoroethoxy)-N-(2-piperidylmethyl)benzamide.

In another aspect of the invention, a method of preparing a 2,5-bis(2,2,2-trifluoroethoxy)-N-(2-piperidylmethyl)benzamide is provided which comprises the following steps. The compound 1,4-dibromobenzene is contacted with an alkali metal 2,2,2-trifluoroethoxide in the presence of cuprous or cupric ion and in a strongly polar solvent comprising 2,2,2-trifluoroethanol to yield 1,4-bis(2,2,2-trifluoroethoxy)benzene. Then, in the presence of a Lewis acid catalyst, the 1,4-bis(2,2,2-trifluoroethoxy)benzene is treated with an acetylation agent under conditions to create 2,5-bis(2,2,2-trifluoroethoxy)acetophenone. The methyl moiety of the acetophenone function of said 2,5-bis(2,2,2-trifluoroethoxy)acetophenone is thereafter replaced to yield 2,5-bis(2,2,2-trifluoroethoxy)benzoic acid. The 2,5-bis(2,2,2-trifluoroethoxy)benzoic acid is then treated with an inorganic chloride to provide 2,5-bis(2,2,2-trifluoroethoxy)benzoic acid chloride. Subsequently, the resultant 2,5-bis(2,2,2-trifluoroethoxy)benzoic acid chloride is contacted with 2-aminomethylpyridine, whereby there is formed a 2,5-bis(2,2,2-trifluoroethoxy)-N-(2-pyridylmethyl)benzamide. Finally, the 2,5-bis(2,2,2-trifluoroethoxy)-N-(2-pyridylmethyl)benzamide is treated with an agent capable of hydrogenation of the aromatic bond in the heterocyclic ring, whereby there is formed a 2,5-bis(2,2,2-trifluoroethoxy)-N-(2-piperidylmethyl)benzamide.

In still another aspect of the invention, a method of preparing a 2,5-bis(2,2,2-trifluoroethoxy)-N-(2-piperidylmethyl)benzamide is provided which comprises the following steps. Hydroquinone is contacted with 2,2,2-trifluoroethyl trifluoromethanesulfonate under conditions to yield 1,4-bis(2,2,2-trifluoroethoxy)-benzene. Then, in the presence of a Lewis acid catalyst, the 1,4-bis(2,2,2-trifluoroethoxy)benzene is treated with an acetylation agent under conditions to create 2,5-bis(2,2,2-trifluoroethoxy)acetophenone. The methyl moiety of the acetophenone function of the 2,5-bis(2,2,2-trifluoroethoxy)acetophenone is thereafter replaced using hypochlorite to yield 2,5-bis(2,2,2-trifluoroethoxy)benzoic acid. Subsequently, the 2,5-bis(2,2,2-trifluoroethoxy)benzoic acid is treated with an inorganic chloride to provide 2,5-bis(2,2,2-trifluoroethoxy)benzoic acid chloride. Finally, the resultant 2,5-bis(2,2,2-trifluoroethoxy)benzoic acid chloride is contacted with 2-aminomethylpiperidine, whereby there is formed 2,5-bis(2,2,2-trifluoroethoxy)-N-(2-piperidylmethyl)benzamide.

In yet another aspect of the invention, a method of preparing a 2,5-bis(2,2,2-trifluoroethoxy)-N-(2-piperidylmethyl)benzamide is provided which comprises the following steps. The compound 1,4-dibromobenzene is contacted with an alkali metal 2,2,2-trifluoroethoxide in the presence of cuprous or cupric ion and in a strongly polar solvent comprising 2,2,2-trifluoroethanol to yield 1,4-bis(2,2,2-trifluoroethoxy)benzene. Then, in the presence of a Lewis acid catalyst, the 1,4-bis(2,2,2-trifluoroethoxy)benzene is treated with an acetylation agent under conditions to create 2,5-bis(2,2,2-trifluoroethoxy)acetophenone. The methyl moiety of the acetophenone function of the 2,5-bis(2,2,2-trifluoroethoxy)acetophenone is thereafter replaced using hypochlorite to yield 2,5-bis(2,2,2-trifluoroethoxy)benzoic acid. Subsequently, the 2,5-bis(2,2,2-trifluoroethoxy)benzoic acid is treated with an inorganic chloride to provide 2,5-bis(2,2,2-trifluoroethoxy)benzoic acid chloride. Finally, the resultant 2,5-bis(2,2,2-trifluoroethoxy)benzoic acid chloride is contacted with 2-aminomethylpiperidine, whereby there is formed 2,5-bis(2,2,2-trifluoroethoxy)-N-(2-piperidylmethyl)benzamide.

The compound 2,5-bis(2,2,2-trifluoroethoxy)-N-(2-piperidylmethyl)benzamide, an antiarrhythmic agent, is disclosed in U.S. Pat. No. 3,900,481.

DETAILED DESCRIPTION

Specifically, the present invention relates to a process for preparing a compound of the formula

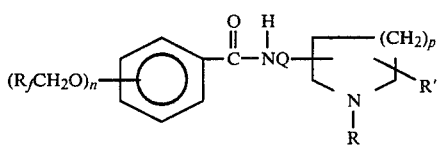

wherein $R_f$ is a perfluoroalkyl radical containing one to three carbon atoms, n is one to three, p is one or two, Q is a carbon to nitrogen bond, methylene or methylmethylene and R and R' are individually hydrogen, methyl or ethyl which comprises (1) reacting a compound of the formula

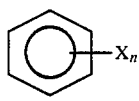

wherein all of the X's are the same and are selected from OH and Br with a suitable alkylating agent of the formula $R_fCH_2O$—A wherein A is $-SO_2CF_3$ or an alkali metal to provide a compound of the formula

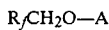, (2) acetylating in the presence of a Lewis acid catalyst to provide a substituted acetophenone of the formula

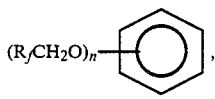

(3) reacting the substituted acetophenone with hyrochlorite to form the corresponding benzoic acid

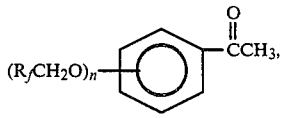

(4) reacting the acid with an inorganic acid chloride to provide the acid chloride

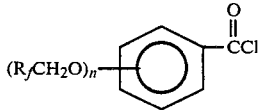

and (5) reacting that product alternatively with a compound of the formula

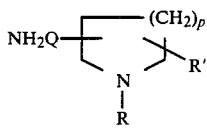

to form the desired product in one step or with a compound of the formula

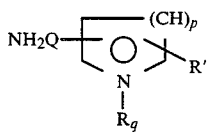

in which q is one when p is one and q is zero when p is two, then reducing to form the desired product.

Preferably, the process is utilized to prepare antiarrhythmic agents in which $R_f$ is $CF_3$, most preferably of the formula

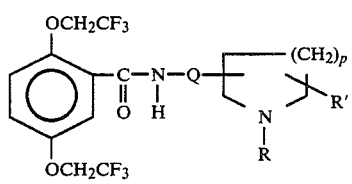

due to the superior properties of such compounds as antiarrhythmics.

The processes which comprise steps (1)–(3) and (3), above, also constitute separate aspects of the overall invention.

The overall process of the invention follows the reaction sequence:

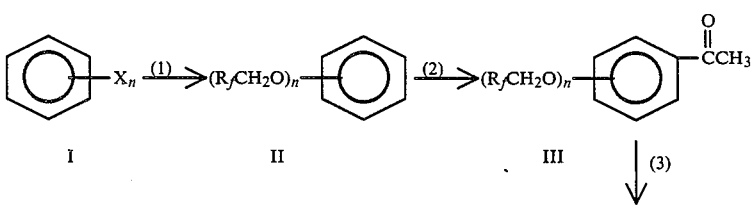

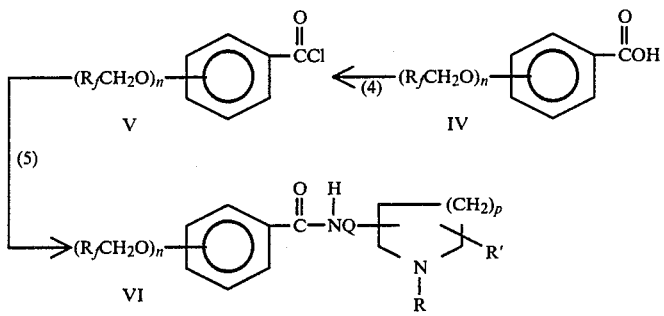

in which the compounds VI are the antiarrhythmic agents previously alluded to.

Preferably, in the foregoing reaction sequence, Q is (1) a carbon-nitrogen bond and is bonded to the 3 position of the pyrrolidine or piperidine ring or (2) a methylene linking group bonded to the 2 position of the piperidine or pyrrolidine ring. Most preferred is the process for preparing the compound of formula VI wherein Q is methylene bonded to the 2 position of a piperidine ring (i.e. in which p is 2) and R and R' are both hydrogen.

In the first step of the process, when X is OH, A is suitably —$SO_2CF_3$ and the reactants are heated together in a solvent such as acetone or N,N-dimethylformamide and in the presence of a base, preferably a weak base such as an alkali metal carbonate, i.e. potassium or sodium carbonate.

When X is Br, the bromobenzene I is reacted with the 1,1-dihydroperfluoroalkoxide ion in a strongly polar solvent mixture at a temperature up to the reflux temperature of the solution in the presence of cuprous or cupric ion to provide the desired product II in good yield. The 1,1-dihydroperfluoroalkoxide ion is obtained from the corresponding alcohol by reaction with a strong base such as sodium hydroxide or preferably sodium hydride. Suitable solvent mixtures include dimethyl sulfoxide, N,N-dimethylacetamide and preferably N,N-dimethylformamide, each with about 10 to 50 percent, and preferably about 20 percent of the 1,1-dihydroperfluoroalcohol (which corresponds to the 1,1-dihydroperfluoroalkoxide ion). Cuprous ion is provided, e.g. by a cuprous halide such as cuprous iodide or cuprous bromide. Cupric ion is provided e.g. by cupric bromide, cupric sulfate or cupric bromide.

In step (2) the 1,1-dihydroperfluoroalkoxy-substituted benzene II produced in the first step is acetylated by reacting under mild conditions with any acetylating agent such as acetyl chloride or acetic anhydride in the presence of a Lewis acid catalyst such as tin chloride, ferric chloride or, preferably, aluminum chloride. The acetylation is carried out in a suitable non-reactive solvent such as a chlorinated hydrocarbon, such as dichloromethane, trichloroethylene or 1,2-dichloroethane, diethyl ether, tetrahydrofuran and the like. Unexpectedly, this reaction provides high yields of the desired substituted acetophenone III.

The reaction of step (3) is most conveniently carried out by adding the acetophenone III to a cold solution of an alkali metal or alkaline earth hydroxide (such as sodium hydroxide, potassium hydroxide or calcium hydroxide) which has been saturated with chlorine to pH 7 (forming the corresponding hypochlorite). The reaction is then facilitated by warming the reaction mixture. A very high yield of the desired 1,1-dihydroperfluoroalkoxy-substituted benzoic acid IV is obtained.

In step (4) the acid is converted to the corresponding acyl chloride by reaction with an inorganic acid chloride such as thionyl chloride, phosphorous trichloride or phosphorous pentachloride (preferably phosphorous trichloride) at reflux with or without a suitable non-reactive solvent such as benzene or toluene or a halogenated hydrocarbon.

The final step of the process may be carried out directly from a saturated ring compound or indirectly from a compound containing an unsaturated ring. Thus, a saturated ring-containing compound such as a 2-aminomethylpiperidine, 2-aminomethylpyrrolidine, 3-aminopiperidine or 3-aminopyrrolidine is reacted with the acid chloride product of step (4) by heating in a non-reactive solvent such as glyme, benzene, toluene or diethyl ether (preferably glyme). Alternatively, a compound such as a 2-aminomethylpyridine, 2-aminomethylpyrrole, 3-aminopyridine or 3-aminopyrrole can be reacted with the acid chloride product of step (4) in the presence of a non-reactive solvent such as toluene or benzene. This mixture is heated at reflux in the presence of an acid acceptor (e.g. a tertiary amine such as triethylamine). The product thereof is then hydrogenated catalytically in the presence of platinum oxide or (preferably) platinum on carbon. The solvent used for this reaction is methanol or a lower alkanoic acid such as (and preferably) glacial acetic acid and the preferred temperature range is 15° to 30° C.

The following examples illustrate the processes of the invention and the preparation of the intermediate product thereof, and are not intended to be limiting on the scope of the invention as described hereinabove.

EXAMPLE 1

Step (1) of the process: A=$SO_2CF_3$ and X=OH.

To a mixture of 2.42 moles (334.4 g.) of potassium carbonates, 2.2 moles (510.6 g.) of 2,2,2-trifluoroethyl trifluoromethanesulfonate in 1.02 liter of acetone is added a solution of 1.0 mole (110 g.) of hydroquinone in 1.1 liter of acetone, slowly over a 2 hour period. The reaction is then heated at reflux for 24 hours, the reaction mixture is evaporated, and 2 liters of chloroform and 2 liters of water are added to the residue. The chloroform layer is separated, the aqueous layer is washed twice with 1 liter of chloroform, and the combined chloroform solution is washed with 1 liter of water. The chloroform solution is dried over magnesium sulfate, then concentrated under vacuum. Hexane is added to the residue and the solid product is collected by filtration and washed with hexane. Additional material is collected from the concentrated residues. A yield of 88 percent, 241 g. of 1,4-bis(2,2,2-trifluoroethoxy)benzene, m.p. 75°–77° C. is obtained.

EXAMPLE 2

Step (1): A=Na and X=Br.

To 0.20 mole (9.6 g.) of 50 percent sodium hydride in 40 ml. of N,N-dimethylformamide is added 40 ml. of 2,2,2-trifluoroethanol followed by 0.034 mole (8.0 g.) of 1,4-dibromobenzene and 0.006 mole (1.0 g) of cuprous iodide. The mixture is heated at its reflux temperature for 4 hours, cooled to about 25° C. and filtered. The residue is washed with N,N-dimethylformamide. The solution is then poured into water, and the precipitate is separated by filtration. The product is dissolved in diethyl ether and filtered and the filtrate solution is evaporated to provide a solid residue which is washed with hexane and dried. The product is 7.3 g. (80 percent) of 1,4-bis(2,2,2-trifluoroethoxy)benzene, m.p. 77° to 79° C.

The reaction is rerun as follows, varying the conditions and proportions of the constituents and utilizing cupric bromide as the catalyst.

To a mixture of 4.8 g. of sodium hydride in 40 ml. of N,N-dimethylformamide is added 20 ml. (27.4 g.) of 2,2,2-trifluoroethanol. To this mixture is added 0.034 mole (8.0 g.) of 1,4-dibromobenzene and 1.0 g. of cupric bromide. The reaction mixture is heated at about 100° C. for two hours, then quenched with ice water. Acidification with hydrochloric acid and filtration produces 9.2 g. (99 percent) of white solid 1,4-bis(2,2,2-trifluoroethoxy)benzene. The structure is confirmed by infrared spectral analysis.

EXAMPLE 3

Step (2) utilizing acetic anhydride as the acetylating agent.

To a mixture of 2.43 moles (324 g.) of aluminum chloride in 648 ml. of dichloromethane is added a solution of 0.88 mole (274 g.) of 1,4-bis(2,2,2-trifluoroethoxy)benzene and 0.97 mole (92 ml.) of acetic anhydride in 880 ml. of dichloromethane over a 3 hour period while maintaining the temperature at above 0° C. The reaction mixture is then heated to its reflux temperature and stirred at reflux for 5 hours. The progress of the reaction is followed using thin-layer chromatography. The reaction mixture is placed in an ice bath and ice and 10 percent hydrochloric acid are added slowly to decompose the aluminum chloride complex. The temperature of the reaction mixture is not allowed to exceed 25° C. The organic phase is separated and washed once with 2 liters of 10 percent hydrochloric acid and then with 2 liters of water. The combined aqueous phase is extracted with several liters of dichloromethane. The organic phase is dried over magnesium sulfate, then evaporated to provide a moist residue. Hexane is added to the residue and the resulting solid is collected by filtration and washed with hexane. Upon drying, 250 g. of light yellow crystalline 2,5-bis(2,2,2-trifluoroethoxy)acetophenone is obtained. The yield is 90 percent, the m.p. is 84° to 86° C.

EXAMPLE 4

A scale up of the run of Example 3.

To a mixture of 4.367 kilograms (32.75 moles) of aluminum chloride and 8.8 liters of dichloromethane at 0° C. is added gradually a solution of 3,267 kilograms of 1,4-bis(2,2,2-trifluoroethoxy)benzene and 1.899 kilograms (13.7 moles) of acetic anhydride in 1.3 liters of dichloromethane. The reaction temperature is maintained to 5° to 10° C. while stirring the mixture for about 16 hours. The reaction mixture is then heated to its reflux temperature and maintained under reflux for 4 hours. The reaction mixture is then acidified with 8.76 kilograms of 10 percent hydrochloric acid. Ice is added to the mixture to maintain the temperature below 20° C. The organic layer is separated and the aqueous layers are extracted several times with dichloromethane. The organic layers are dried, then evaporated to provide a residue which is triturated with hexane to provide a yellow solid product. Two crops of product are obtained providing a total yield of 3.088 kilograms of 2,5-bis(2,2,2-trifluoroethoxy)acetophenone, m.p. 84° to 88° C., yield 82 percent.

EXAMPLE 5

Step (2) utilizing acetyl chloride as the acetylating agent.

To a mixture of 0.022 mole (2.8 g.) of aluminum chloride and 100 ml. of 1,2-dichloroethane is added dropwise at 25° C. a solution of 0.020 mole (5.6 g.) of 2,5-trifluoroethoxy)benzene and 0.022 mole (1.7 g.) of acetyl chloride in 20 ml. of 1,2-dichloroethane. After stirring for 4 hours the reaction mixture is washed with ice water and hydrochloric acid and the organic layer is dried. Evaporation produces a residue which is recrystallized from hexane to provide 4.1 g. (71 percent) of pale yellow needles of 2,5-bis(2,2,2-trifluoroethoxy)acetophenone (as verified by infrared spectral analysis).

EXAMPLE 6

Step (3).

To a solution of 7.3 moles (292 g.) of sodium hydroxide in 600 ml. of water is added ice to make the total volume of 1.75 liters. Chlorine gas is passed into the solution while maintaining the temperature below 10° C. until it is neutral to litmus, and 2.19 moles (87.6 g.) of sodium hydroxide dissolved in 200 ml. of water is added. The combined solution is warmed to 50° C., and 0.73 mole (230 g.) of 2,5-bis(2,2,2-trifluoroethoxy)acetophenone is added slowly. The reaction mixture is stirred while heating until an exotherm begins about 75° C. and is thereafter maintained at about 80° C. by cooling. The mixture is stirred for about 16 hours at about 80° to 90° C. while monitoring the extent of the reaction by thin-layer chromatography. The excess hypochlorite is then destroyed by adding 75 g. of sodium bisulfite in 250 ml. of water, and the mixture is cooled to about 25° C. and carefully acidified with 10 percent hydrochloric acid. The light yellow solid product is collected by filtration, washed with water, and dried. A 94.5 percent yield of 2,5-bis(2,2,2-trifluoroethoxy)benzoic acid, m.p. 120° to 122° C., is obtained.

EXAMPLE 7

Step (4).

To a solution of 0.688 mole (219 g.) of 2,5-bis(2,2,2-trifluoroethoxy)benzoic acid in 657 ml. of benzene is added 1.376M. (100.4 ml.) of thionyl chloride slowly over 1 hour while heating to about 60° C. The mixture is then heated at reflux for about 8 hours, then evaporated to provide the desired product, 2,5-bis(2,2,2-trifluoroethoxy)benzoic acid chloride as a residue. The structure is verified by means of infrared spectral analysis.

EXAMPLE 8

Step (5) carried out in two reactions.

To a mixture of 0.77 mole (83.3 g.) of 2-aminomethylpyridine, 0.77 mole (106.7 ml.) of triethylamine and 300 ml. of benzene is added 0.70 mole (236 g.) of 2,5-bis(2,2,2-trifluoroethoxy)benzoic acid chloride in 472 ml. of benzene over 1 hour.

The reaction mixture is stirred for about 16 hours at 25° C., refluxed for one hour, then washed twice with 2 liters of water. The aqueous phase is washed with 2 liters of benzene, and the combined organic phases are dried over magnesium sulfate, then evaporated under vacuum. Recrystallization from a mixture of benzene and hexane gives 240 g., 86 percent, of off-white 2,5-bis(2,2,2-trifluoroethoxy)-N-(2-pyridylmethyl)benzamide, m.p. 100° to 102° C.

A mixture of 0.33 mole (134.7 g.) 2,5-bis(2,2,2-trifluoroethoxy)-N-(2-pyridylmethyl)benzamide, 1.347 liter of glacial acetic acid and 13.5 g. of 5 percent platinum on carbon is reduced in a Parr apparatus at a pressure of about 10 pounds of hydrogen at room temperature. The reaction is complete in 6–7 hours. The reaction mixture is filtered and the catalyst is washed with isopropyl alcohol. The solution and washings are evaporated to provide a residue. Hexane is added to the residue and the resulting white solid is collected and recrystallized from a mixture of acetone and hexane. A 71 percent yield of 2,5-bis(2,2,2-trifluoroethoxy)-N-(2-piperidylmethyl)benzamide acetate, m.p. 150° to 152° C., is obtained. By concentrating the residual liquid an additional 18 percent of product is obtained as a second crop with a melting point of 148°–150° C.

What is claimed is:

1. A method of preparing a 2,5-bis(2,2,2-trifluoroethoxy)-N-(2-piperidylmethyl)-benzamide which comprises:
    (a) contacting 1,4-dibromobenzene with an alkali metal 2,2,2-trifluoroethoxide in the presence of cuprous or cupric ion and in a strongly polar solvent comprising 2,2,2-trifluoroethanol whereby 1,4-bis(2,2,2-trifluoroethoxy)benzene is formed;
    (b) in the presence of a Lewis acid catalyst, treating said 1,4-bis(2,2,2-trifluoroethoxy)benzene with an acetylation agent under conditions to create 2,5-bis(2,2,2-trifluoroethoxy)acetophenone:
    (c) replacing the methyl moiety of the acetophenone function of said 2,5-bis(2,2,2-trifluoroethoxy)acetophenone to yield 2,5-bis(2,2,2-trifluoroethoxy)benzoic acid;
    (d) treating said 2,5-bis(2,2,2-trifluoroethoxy)benzoic acid with an inorganic chloride to provide 2,5-bis(2,2,2-trifluoroethoxy)benzoic acid chloride;
    (e) contacting the resultant 2,5-bis(2,2,2-trifluoroethoxy)benzoic acid chloride with 2-aminomethylpyridine, whereby there is formed 2,5-bis(2,2,2-trifluoroethoxy)-N-(2-pyridylmethyl)benzamide;
    (f) treating said 2,5-bis(2,2,2-trifluoroethoxy)-N-(2-pyridylmethyl)benzamide with an agent capable of hydrogenation of the aromatic bond in the heterocyclic ring, whereby there is formed a 2,5-bis(2,2,2-trifluoroethoxy)-N-(2-piperidylmethyl)benzamide.

2. A method of claim 1 wherein said 2,5-bis(2,2,2-trifluoroethoxy)-N-(2-piperidylmethyl)benzamide is recovered in the form of its acetate.

3. A method of preparing a 2,5-bis(2,2,2-trifluoroethoxy)-N-(2-piperidylmethyl)benzamide which comprises:
    (a) contacting 1,4-dibromobenzene with an alkali metal 2,2,2-trifluoroethoxide in the presence of cuprous or cupric ion and in a strongly polar solvent comprising 2,2,2-trifluoroethanol to yield 1,4-bis(2,2,2-trifluoroethoxy)benzene;
    (b) in the presence of a Lewis acid catalyst, treating said 1,4-bis(2,2,2-trifluoroethoxy)benzene with an acetylation agent under conditions to create 2,5-bis(2,2,2-trifluoroethoxy)acetophenone;
    (c) replacing the methyl moiety of the acetophenone function of said 2,5-bis(2,2,2-trifluoroethoxy)acetophenone using hypochlorite to yield 2,5-bis(2,2,2-trifluoroethoxy)benzoic acid;
    (d) treating said 2,5-bis(2,2,2-trifluoroethoxy)benzoic acid with an inorganic chloride to provide 2,5-bis(2,2,2-trifluoroethoxy)benzoic acid chloride;
    (e) contacting the resultant 2,5-bis(2,2,2-trifluoroethoxy)benzoic acid chloride with 2-aminomethylpiperidine, whereby there is formed 2,5-bis(2,2,2-trifluoroethoxy)-N-(2-piperidylmethyl)benzamide.

4. A method of claim 3 wherein said 2,5-bis(2,2,2-trifluoroethoxy)-N-(2-piperidylmethyl)benzamide is recovered in the form of its acetate.

* * * * *